US012573497B2

(12) United States Patent
Sharma et al.

(10) Patent No.: US 12,573,497 B2
(45) Date of Patent: Mar. 10, 2026

(54) SYSTEMS AND METHODS FOR AUTOMATING WORKFLOWS

(71) Applicant: GE Precision Healthcare LLC, Wauwatosa, WI (US)

(72) Inventors: Ashish Kumar Sharma, Bangalore (IN); Nithya Ramachandran, Bangalore (IN); Pavankumar Neelaiah Radha, Mysuru (IN)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 210 days.

(21) Appl. No.: 18/085,812

(22) Filed: Dec. 21, 2022

(65) Prior Publication Data

US 2024/0212829 A1     Jun. 27, 2024

(51) Int. Cl.
*G16H 30/20*          (2018.01)
(52) U.S. Cl.
CPC ................................... *G16H 30/20* (2018.01)
(58) Field of Classification Search
CPC .................................................... G16H 30/20
See application file for complete search history.

(56) References Cited

U.S. PATENT DOCUMENTS

| | | |
|---|---|---|
| 6,782,370 B1 | 8/2004 | Stack |
| 7,240,353 B2 | 7/2007 | Lau et al. |

| | | | | |
|---|---|---|---|---|
| 2011/0113361 | A1* | 5/2011 | Bhatt | H04N 1/0044 |
| | | | | 345/643 |
| 2013/0120439 | A1* | 5/2013 | Harris | G11B 27/34 |
| | | | | 345/619 |
| 2013/0129165 | A1 | 5/2013 | Dekel et al. | |
| 2015/0222576 | A1* | 8/2015 | Anderson | G06F 9/44 |
| | | | | 715/752 |
| 2016/0125155 | A1* | 5/2016 | Shelter | H04M 3/567 |
| | | | | 705/2 |
| 2018/0260081 | A1* | 9/2018 | Beaudoin | G06F 3/04817 |
| 2019/0391736 | A1* | 12/2019 | Tanaka | G06F 3/041 |
| 2020/0194034 | A1* | 6/2020 | Akagi | G06T 7/0016 |
| 2021/0027883 | A1 | 1/2021 | Kumar et al. | |
| 2021/0358524 | A1* | 11/2021 | Zheng | G11B 27/036 |

FOREIGN PATENT DOCUMENTS

| | | |
|---|---|---|
| EP | 3506279 A1 | 7/2019 |

* cited by examiner

*Primary Examiner* — Steven G.S. Sanghera
(74) *Attorney, Agent, or Firm* — Fletcher Yoder, P.C.

(57)          ABSTRACT

A system may include a database comprising historical workflow data, a plurality of workflow videos, and a plurality of video fragments, a review station in communication with the database, and a workflow application comprising routines executed by a processor of the review station and communicatively coupled to the database. The review station may concurrently display image data and one or more workflow videos of the plurality of workflow videos and receive an input corresponding to an action performed on the image data. The workflow application may determine whether the action corresponds to an expected action and update the one or more workflow videos displayed on the review station based on the action.

19 Claims, 9 Drawing Sheets

| Workstation | 10 |
| Communication | 12 |
| Processor | 14 |
| Memory | APP | 16 / 26 |
| Storage | 20 |
| I/O Ports | 22 |
| Display | 24 |

Network ⟶ 28

Database ⟶ 30

| | 10 |
| 40 | Actions panel | 46 |
| 42 | Viewing space | Workflow video 1 | 44a |
| | | Workflow video 2 | 44b |
| | | Workflow video 3 | 44c |

80

Identify an action ~ 82

Identify one or more workflow videos in a database based on the action ~ 84

Update a GUI with the one or more workflow videos ~ 86

SYSTEMS AND METHODS FOR AUTOMATING WORKFLOWS

BACKGROUND

The subject matter disclosed herein relates to medical imaging and, more particularly, to systems and methods for generating and utilizing actionable workflow videos to automatically perform or facilitate the performance of two or more actions.

Non-invasive imaging technologies allow images of the internal structures of features of a subject (e.g., patient, manufactured good, baggage, package, or passenger) to be obtained non-invasively. In particular, such non-invasive imaging technologies rely on various physical principles, such as the differential transmission of X-rays through the target volume or the reflection of acoustic waves, to acquire data and to construct images or otherwise represent the internal features of the subject. By way of example, in X-ray based imaging technologies, signals representative of an amount or an intensity of radiation may be collected and the signals may then be processed to generate an image that may be displayed for review.

When reviewing the image, a user may perform one or more actions on and/or with the image to make an assessment, provide feedback, and/or make a diagnosis. For example, the user may label areas of the image that may need reprocessing. In another example, the user may make annotations on the image, save an annotated image, or generate a report based on the annotated image. The user may perform multiple actions; in certain instances, the user may perform a sequence of actions, referred to herein as a "workflow." For example, the user may save an annotated image, generate a report based on the annotated image, and send the annotated image within an institution. That is, the user may manually perform each action, which may introduce human error. Moreover, having to manually perform the actions may be time-consuming for the operator and increase costs associated with making a diagnosis. Thus, improvements for optimizing workflows are desired decrease turn-around time, decrease operational costs, and improve quality of service delivery.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In an embodiment, a system may include a database a radiology review station in communication with the database, and a workflow application. The database may include historical workflow data associated with the review of radiology images, a plurality of workflow videos, and a plurality of frames. The review station may concurrently display a clinical image and one or more workflow videos of the plurality of workflow videos and receive an input corresponding to an action performed on the clinical image during a review of the clinical image. The workflow application may include routines executed by a processor of the radiology review station and communicatively coupled to the database. The workflow application may update the one or more workflow videos displayed on the radiology review station based on the action.

In an embodiment, a method may include concurrently displaying, via a processor, medical image and one or more workflow videos based on a user profile, receiving an input of an action performed on or to be performed on the medical image, and updating the one or more workflow videos concurrently displayed with the medical image based on the action.

In an embodiment, a non-transitory, computer-readable medium comprising computer-readable code, that when executed by one or more processors, causes the one or more processors to perform operations including concurrently displaying a medical image and a list of workflow videos based on a user profile, receiving a first input of an action performed on or with the medical image, and updating, via the processor, the list of workflow videos concurrently displayed with the medical image based on the action.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figures 1, 2:
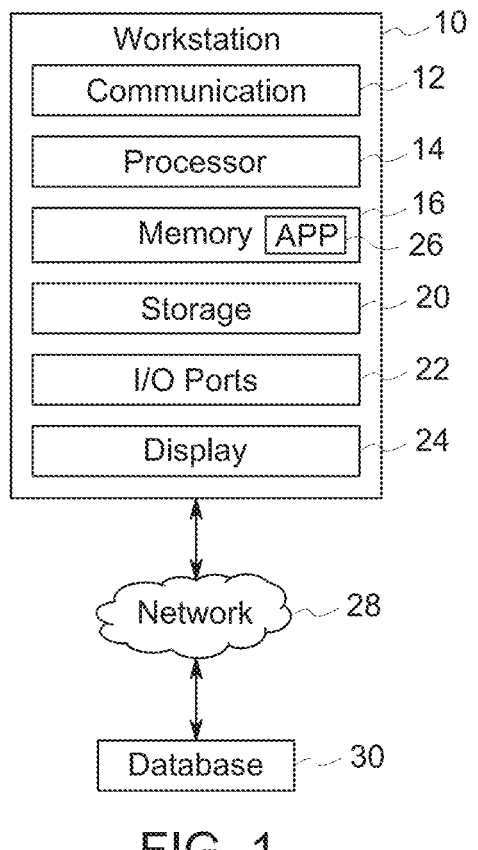
FIG. 1 illustrates a block diagram of a review station including a workflow application communicatively coupled to a database, in accordance with embodiments described herein.
FIG. 2 illustrates a schematic diagram of a graphical user interface (GUI) generated by the workflow application for display on the review station of FIG. 1, in accordance with embodiments described herein.

One or more specific embodiments of the present disclosure are described above. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as workflows related to editing and exporting photography images (e.g., photoshopping images), microscopy images (e.g., optical microscopy, electronic microscopy, scanning probe microscopy), images for inspection of objects (e.g., security screening for packages, boxes, luggage), images for industrial inspections, and so on. The present approaches may also be utilized for workflows for video calling applications (e.g., starting a meeting, recording the meeting, switching on camera), graphic design (e.g., selecting a template, selecting a font, applying a background color), and so on.

By way of example, a radiology workflow may include actions such as ordering, annotating, scheduling, image acquisition, storage, and viewing activities associated with radiology exams. Following image acquisition, a user (e.g., radiologist) may perform image and data interpretation to determine a diagnosis, future treatments, and/or reporting of results. For example, the user may annotate or label the image and adjust one or more parameters (e.g., contrast) of the image to prepare the image for a different department (e.g., surgery) for shared decision making. Further, the user may save the image with the annotations to a patient file or image archive and/or may print the image for future use. The user may manually perform each action by selecting a button from a toolbar and performing the action. However, certain actions may be repeatedly performed by the user, thereby increasing read time. Furthermore, the user may be prone to human error when performing the actions. Thus, operational costs associated with reading the images may increase.

Embodiments of the present disclosure are directed to a workflow application integrated with a workstation (e.g., review station) to decrease read time and error by sequentially performing two or more actions on the image without human intervention. For example, the software workflow application may generate workflow videos illustrating two or more actions (e.g., workflow actions) to be sequentially performed by the application. The workflow application may populate a graphical user interface (GUI) displayed on the workstation with the workflow videos. The user may view the workflow views and select a workflow video to automate two or more actions. The workflow application may perform the actions in response to receiving an input (e.g., user input). In this manner, the user may decrease a read time for each image reviewed and may simultaneously decrease the likelihood of human error.

The workflow application may learn, such as via machine-learning, actions repeatedly performed by the user. For example, the workflow application may monitor actions of a respective user (or of a set of users affiliated with a respective organization) and identify workflows that are routinely performed. For example, the workflow application may identify the user saving an annotated image followed by sending the annotated image to a different department at the end of each review. The workflow application may create a workflow video with a first frame associated with saving the image and a second frame with sending the image. The workflow application may tag the workflow video based on the actions and display the workflow video at the end of each review. In this way, the workflow application may prioritize workflow videos based on user preferences and/or user workflow styles, thereby reducing a read time. Moreover, automating workflows for multiple reviews may greatly improve turnaround time or reduce read time, reduce human error, and improve overall quality of service delivered.

With the preceding in mind, FIG. 1 illustrates an embodiment of a workstation 10 for acquiring and processing image data, in accordance with aspects of the present disclosure. The workstation 10 may receive raw or pre-processed image data from one or more data sources and process the signals into image data via signal processing techniques, machine-learning routines, artificial intelligence, and so on. The workstation 10 may also receive processed or pre-processed image data and perform image visualization techniques. For example, an operator (e.g., radiologist) may use the workstation 10 to view images, annotate, analyze, store, print, send, or otherwise manipulate the image data. To this end, the workstation 10 may include any suitable computer device, such as a general-purpose personal computer, a laptop computer, a tablet computer, a mobile computer, and the like that includes specific computer-readable instructions in accordance with present embodiments. In an embodiment, the workstation 10 may include a picture archiving and communications system (PACS) that may store and transmit information captured by medical imaging. For example, the information may include image data such as computed tomography (CT), X-Ray, (positron emission tomography (PET), (single-photon emission computed tomography (SPECT), tomosynthesis, mammography, fluoroscopy, magnetic resonance imaging (MRI), and so on. The PACS may in turn be coupled to a remote client, radiology department information system (RIS), hospital information system (HIS) or to an internal or external network, so that others at different locations may gain access to the raw or processed image data.

The workstation 10 may include various types of components that may assist the workstation 10 in performing various types of tasks and operations. For example, the workstation 10 may include a communication component 12, a processor 14, a memory 16, a storage 20, input/output (I/O) ports 22, a display 24, and the like. During operation, the memory 16 may store a workflow application 26 that, when executed by the processor 14, monitors and stores workflow data (e.g., user workflows over time), creates workflow videos, identifies workflow videos for display, and executes the workflow associated with a selected workflow video. To this end, the workflow application 26 may include, access, or be updated using a machine-learning routine that may be trained based on user workflows from users within a department, an institution, a local region, or the like. As such, in some embodiments the workflow application 26 may not directly analyze the image data and/or learn information regarding the image data to keep patient information confidential.

The communication component 12 may be a wireless or wired communication component that may facilitate communication between the workstation 10 and various other workstations via a network, the Internet, or the like. For example, the communication component 12 may send or receive images from other workstations.

The processor 14 may be any type of computer processor or microprocessor capable of executing computer-executable code. For example, the processor 14 may be configured to receive user input, such as actions performed by the operator, indications to perform a workflow, scanning parameters, or the like. Thus, the operator may select image data for viewing on the workstation 10, perform one or more actions (e.g., annotate, schedule, send) on the image data, and/or otherwise operate the workstation 10. Further, the processor 14 may be communicatively coupled to other output devices, which may include standard or special purpose computer monitors associated with the processor 14. One or more workstations 10 may be communicatively coupled for requesting examinations, viewing images, sending images, storing images, and so forth. In general, displays, printers, workstations, and similar devices supplied with or within the system may be local to the data acquisition components, or maybe remote from these components, such as elsewhere within an institution (e.g., hospital, school), or in an entirely different location, linked to the workstation 10 via one or more configurable networks, such as the Internet, virtual private networks, and so forth. The processor 14 may also include multiple processors that may perform the operations described below.

The memory 16 and the storage 20 may be any suitable articles of manufacture that can serve as media to store processor-executable code, data, or the like. These articles of manufacture may represent computer-readable media (e.g., any suitable form of short-term memory or long-term storage) that may store the processor-executable code used by the processor 14 to perform the presently disclosed techniques. As used herein, applications may include any suitable computer software or program that may be installed onto the workstation 10 and executed by the processor 14. The memory 16 and the storage 20 may represent non-transitory (e.g., physical) computer-readable media (e.g., any suitable form of memory or storage) that may store the processor-executable code used by the processor 14 to perform various techniques described herein. For example, the memory 16 may include machine-learning routines configured to learn the operator's preferred workflows for reading image data.

The memory 16 may store the workflow application 26, such as for execution by the processor 14. The application 26, when executed, may automatically perform a workflow on or with the image data. For example, the application 26 may perform three actions associated with the workflow video selected by the operator. In another example, the application 26 may annotate the image data, save the annotated image data, and send the image data to another department within the institution based on preferences of the operator. In another example, the application 26 may adjust a contrast of the image data, label the image data, and store the image data to a database or a cloud server based on preferences of the operation. Indeed, historical workflow data may be utilized to train the machine-learning routines such that the application 26 may predict subsequent workflows of the operator and present the workflows to reduce read time. Additionally or alternatively, the application 26 may display the workflow videos based on preferences of the operator and generate new workflow videos.

Returning to the workstation 10, the I/O ports 22 may be interfaces that may couple to other peripheral components such as input devices (e.g., keyboard, mouse), sensors, input/output (I/O) modules, and the like. The display 24 may operate as a human machine interface (HMI) to depict visualizations associated with software or executable code being processed by the processor 14. In one embodiment, the display 24 may be a touch display capable of receiving inputs from a user of the workstation 10. The display 24 may be any suitable type of display, such as a liquid crystal display (LCD), plasma display, or an organic light emitting diode (OLED) display, for example. Additionally, in one embodiment, the display 24 may be provided in conjunction with a touch-sensitive mechanism (e.g., a touch screen) that may function as part of a control interface for the workstation 10.

It should be noted that the workstation 10 should not be limited to include the components described above. Instead, the components described above with regard to the workstation 10 are examples, and the workstation 10 may include additional or fewer components relative to the illustrated embodiment. For example, the processor 14 and the memory 16 may be provided collectively within the workstation 10.

In certain embodiments, the workstation 10 may be communicatively coupled to a network 28, which may include collections of workstations, the Internet, an Intranet system, or the like. The network 28 may facilitate communication between the workstation 10 and various other data sources. For example, the network 28 may facilitate communication between a workstation 10 located on the surgery floor and a workstation 10 located in the radiology floor. In another example, the network 28 may facilitate communication between the workstation 10 and a database 30. In certain instances, the database 30 may store image data (e.g., raw or processed). The database 30 may also store workflow data such as frequent actions performed by the operator, sequences of actions performed, preferences of the operator, historical workflow data of the operator, and so on. In an embodiment, the database 30 may be a cloud server that stores historical workflow data of multiple operators. The database 30 may also store pre-made workflow videos, new workflow videos, video fragments, workflow animations, tags, and so on. In certain instances, the workflow data may be associated with an operator profile, an institution profile, a department profile, or the like within the database. In this way, preferences across the institution and/or a department may be considered by the workflow application 26 when identifying a workflow video and/or prioritizing the list of workflow videos. Furthermore, the application 26 may utilize attributes (e.g., department, credentials, seniority) of the operator profile to identify the workflow video and/or prioritize the list of workflow videos. For example, an operator may prefer to print the image data prior to saving the image data while a different operator may prefer to save the image data then send the image data. The application 26 may track such actions and associate the actions with the operator profile to customize the presented workflow videos for each operator. Such data from the database 30 may be used by the workstation 10 to store one or more video fragments for workflow videos, one or more workflow videos, and user inputs.

Although the database 30 is illustrated as separate from the workstation 10, in an embodiment, the database 30 may be a component within the workstation 10. In an embodiment, the database 30 may be local to the workstation 10 and store workflow data of the operators using the workstation 10. In other embodiments, as described herein, the database 30 may be a cloud service or a remote database communicatively coupled to the workstation 10 via the network 28.

FIG. 2 is a schematic illustration of a graphic user interface (GUI) 40 displayed on the workstation 10, in accordance with aspects of the present disclosure. For example, the display 24 of the workstation 10 may display the GUI 40 and the operator may select a workflow video for the application 26 to perform the associated actions. The GUI 40 may include a viewing space 42 that displays the image data for review, a list of workflow videos 44, and an action panel 46. The operator may utilize the GUI 40 to review image data; and in certain instances, the operator may select a workflow video to automate two or more actions to improve workflow operations, reduce read time, and human error.

The viewing space 42 may display image data selected by the operator for review. For example, the operator may use the actions panel 46 to open a folder containing image data for review. As described herein, the image data may be 2D image data (e.g., X-Ray, mammography, fluoroscopy), volumetric image data (e.g., MRI, CT, SPECT, PET, tomosynthesis), or the like. The operator may select the image data for review and the image data may be populated in the viewing space 42.

In an embodiment, the operator may use the actions panel 46 to perform one or more actions to and/or with the image data. For example, the actions panel 46 may include buttons corresponding to actions the operator may perform. The buttons may include actions for opening image data, annotating the image data, labeling the image data, saving the image data, sending the image data, generating a report, and so on. The operator may select a button and to perform the action associated with the button. For example, the operator may select the annotate button and draw a line on the image data. The operator may select the annotate button again to draw another line on the image data. Then, the operator may select the label button to label the selected region for reprocessing by the workstation 10. To this end, the operator may select the reprocessing button to command the workstation 10 to perform the action. As described herein, manually selecting and commanding the workstation 10 to perform each action may be time-consuming. Furthermore, the operator may be prone to human error, as such quality of service delivered may decrease.

The GUI 40 may also include a list of workflow videos 44 that may correspond to one or more actions to be automatically performed by the workflow application 26 without human intervention. As further described with respect to FIG. 3, the workflow videos 44 may include pictorial representations (e.g., stock images, still images, screen captures, video fragments) of actions performed to or with the image data by the application 26. For example, the workflow video 44 may include four frames (or sequences of frames) corresponding to four actions the application 26 may perform. As used herein, a "frame" may be understood to be a single image of a video (which may be displayed once or multiple times as part of playing the video) or a segment or "snippet" of the video showing the same or related images corresponding to the content associated with the segment. The workflow video 44 may include a first frame displaying a save action, a second frame displaying a print action, a third frame displaying a send action, and a fourth frame displaying an exit action. In this way, the operator may select a workflow video 44 to perform the four actions rather than using the action panel 46 to manually perform each action.

The application 26 may update the list of workflow videos 44 as the operator reviews the image data. For example, if the operator performs a first action, the application 26 may identify one or more workflow videos 44 that may be a desired next action for the operator. As such, the application 26 may update the workflow videos displayed in the GUI 40. In this way, the application 26 may predict the actions of the operator and reduce read time by presenting actionable workflow videos.

The list of workflow videos 44 may be ordered (e.g., prioritized) via machine learning, such as to correspond to the operator's preferences. By way of example, a first workflow video (e.g., workflow video 1) 44a may be a workflow frequently used by the operator. A second workflow video (e.g., workflow video 2) 44b may be a workflow sometimes used by the operator and the third workflow video (e.g., workflow video 3) 44c may be a new workflow video or a workflow rarely used by the operator. In certain instances, the workflow video 2 and/or the workflow video 3 may be newly generated workflow videos based actions performed in a recent study by the operator. In other words, the first workflow video 44a may be a highest probability for selection by the operator, the second workflow video 44b may have a lower likelihood of selection, and the third workflow video 44c may have the lowest likelihood of selection of the displayed workflow videos.

By way of example, the operator (e.g., radiologist) may be reviewing image data to generate a report for a different department. The operator may have a mammogram displayed in the viewing space 42. The operator may mark (e.g., annotate) areas of interest, areas that need to be reprocessed because a different processing technique may give a better image, and areas that need to be reimaged. In response to the annotations, the workflow application 26 may predict actions for the remainder of the review. The workflow application 26 may identify one or more workflow videos 44 in the database 30 based on the performed actions and the user profile. For example, the workflow videos 44 may include options for forwarding the image data to a second reviewer, saving the annotated image data, or the like. Presenting the workflow in a video format may allow the operator to quickly and easily understand the sequence of actions to be performed and have the actions performed with one selection, rather than multiple selections needed to manually perform the actions. Predicting the subsequent actions of the operator may allow the application 26 to present relevant workflow videos 44 and completing the workflow in response to receiving a user input may reduce read time for the operator.

In an embodiment, the operator may concurrently review two or more images (e.g., image data) in two or more graphical user interfaces. For example, the operator may interact with a first GUI to execute a first workflow video on a first image. While the application executes the actions associated with the first workflow video, the operator may interact with a second GUI to execute a second workflow video on a second image, and so on. In this way, the application may concurrently perform image reviews on multiple images, thereby reducing an amount of time needed to perform image reviews and/or make a diagnosis.

While the illustrated GUI 40 includes three workflow videos (or thumbnail views of workflow videos) 44a-c in the list of workflow videos, any suitable number of workflow videos 44 may be displayed on the GUI 40. For example, the GUI 40 may display 1, 2, 4, 5, 6, or more workflow videos or corresponding thumbnail views. Furthermore, the workflow videos 44 may include any suitable number of frames corresponding to actions performed by the application 26. For example, the workflow video 44 may include 2, 4, 5, 6, 7, 10, 20, 30, or more actions to be performed by the workflow application 26.

Figure 3:
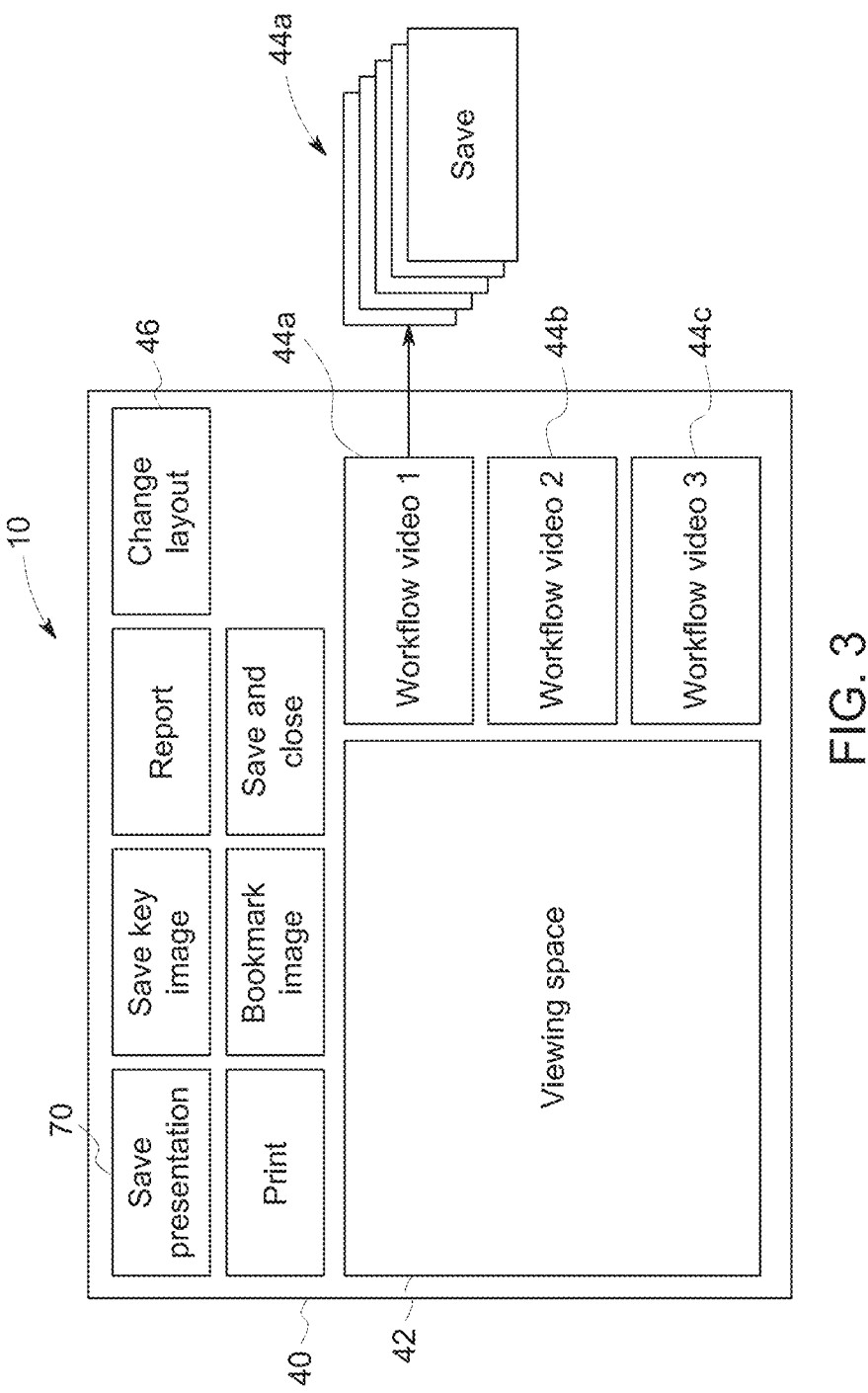
FIG. 3 illustrates a schematic diagram of the GUI of FIG. 2 including one or more actions and a workflow video, in accordance with embodiments described herein.

FIG. 3 is a schematic illustration of GUI 40 displayed on the workstation 10, in accordance with aspects of the present disclosure. The illustrated GUI 40 is substantially similar to the GUI 40 described with respect to FIG. 2, except that the illustrated GUI 40 includes a pop-up displaying the actions associated with the first workflow video 44a. In certain instances, the action panel 46 may be populated with buttons 70 associated with actions, such as save a presentation, save key image, report, change layout, print, bookmark image, save and close.

The operator may use an input device connected to the I/O ports 22 to view the actions associated with the workflow video 44 prior to selecting the view. For example, the operator may move a mouse to hover over the first workflow video 44 for a threshold amount of time to activate the video. The application 26 may initiate the workflow video 44 in response to the operator input (e.g., hovering). That is, the workflow video 44 may display each frame or select frames of the workflow video 44. For example, the first workflow video 44a may include five frames associated with five actions performed by the workflow application 26, if selected. The first workflow video 44 may display a first frame for an amount of time (e.g., 10 seconds, 30 seconds, 1 minute, etc.), followed by a second frame, a third frame, a fourth frame, and a fifth frame. In an embodiment, the frames may be continuously displayed until the operator moves the mouse from over the workflow video 44. In other embodiments, the sequence of frames may be displayed once. Still in another embodiment, the workflow video 44 may display a sequence of actions in strings of text. For example, each frame 60 may include the caption 64 and may not include the pictorial representation 62. As such, the operator may get a snapshot of the actions performed in response to selecting the workflow video 44.

Figure 4:
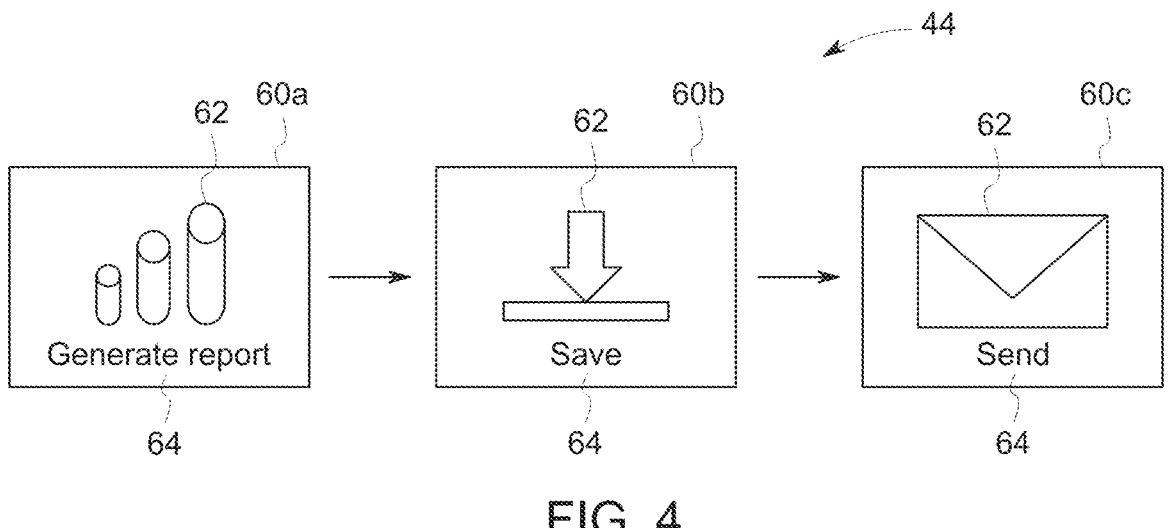
FIG. 4 illustrates a schematic diagram of a workflow video created by the workflow application for display on the review station of FIG. 1, in accordance with embodiments described herein.

FIG. 4 is a schematic illustration of the pictorial representations that might make up each frame of a workflow video 44, in accordance with aspects of the present disclosure. For example, the pictorial representations may be a still image, such as a clip-art, a generic image, a stock image, or the like that may be associated with the action to be performed. In another example, the pictorial representations may be a moving image or an animation, such as a video or sub-video, of the action. Still in another example, the pictorial representations may be a combination of a still image and an animation. The workflow video 44 may include any suitable combination of still images or video fragments to convey the workflow to the operator.

The workflow video 44 may include any suitable number of actions for the application 26 to perform. To this end, the workflow video 44 may include frames 60 with a pictorial representation 62, and a caption 64. In the illustrated example, the pictorial representation 62 may be a still image (e.g., "out-of-the-box" or canned image), such as a stock image, a clip-art image, an icon, or the like. In other embodiments, the pictorial representation 62 may be a screen capture, such as an image of the current image data displayed in the viewing space 42. In the illustrated example, the workflow video 44 may include three frames 60. A first frame 60a may illustrate generating a report. In an embodiment, the pictorial representation 62 may be a still image (e.g., canned image) of a graph and the caption 64 may read "GENERATE REPORT." The second frame 60b may illustrate saving the image data and the corresponding pictorial representation 62 may be a still image illustrating a down arrow and the caption 64 may read "SAVE." A third frame may illustrate sending the image data and the corresponding pictorial representation 62 may be an envelope and the caption 64 may read "SEND." As such, when the operator hovers over the workflow video 44, the workflow video 44 may sequentially display each frame 60. In this way, the operator may understand the actions associated with the workflow video 44 or the actions sequentially performed by the application 26 in response to selecting the workflow video 44.

In certain instances, the frames 60 may be premade or designed during prior to delivery to the customer (e.g., during manufacture) and the frames 60 may be updated and/or changed during use, such as during use at the customer site. For example, the pictorial representations 62 may be a generic representation of the action. One pictorial representation 62 may be created for each action that may be performed by the workflow application 26. In other words, each button of the action panel 46 may have an associated pictorial representation 62. Strings of text may be stored in the database 30 and later used to create the caption 64. In certain instances, the frames 60 including the pictorial representation 62 and the caption 64 may be stored in the database 30. The frames 60 may be created and stored in the database 30 prior to the workstation 10 being shipped to the operator. As such, the application 26 may create workflow videos as soon as the workstation 10 is installed. Furthermore, the frames 60, the pictorial representations 62, and/or the captions 64 may be periodically updated and saved to the database 30.

As the operator uses the workstation 10, the application 26 may create new frames 60, pictorial representations 62, and/or captions 64. For example, the application 26 may screen capture actions performed and save the action as a frame 60 in the database 30. In another example, the application 26 may create frames 60 in real-time or near real-time using the image data being displayed in the viewing space 42. As further described with respect to FIG. 4, the application 26 may retrieve the image data and populate each frame 60 with the image data and an animation of a workflow action. The application 26 may tag (e.g., label) the frame 60 and/or the pictorial representation 62 with the caption 64. When generating a new workflow video, the application 26 may use the screen capture as the frame 60 and/or pictorial representation 62 to depict the action to be performed. In this way, the workflow videos 44 may be personalized to the operator and/or the workflow station.

By displaying the workflow as a video format, the operator may quickly and easily understand the actions and reduce an amount of time to review the image data. Further, the application 26 may sequentially perform the actions in response to receiving a selection of a workflow video, thereby saving the operator time that might be spent to manually perform the actions.

Figure 5:
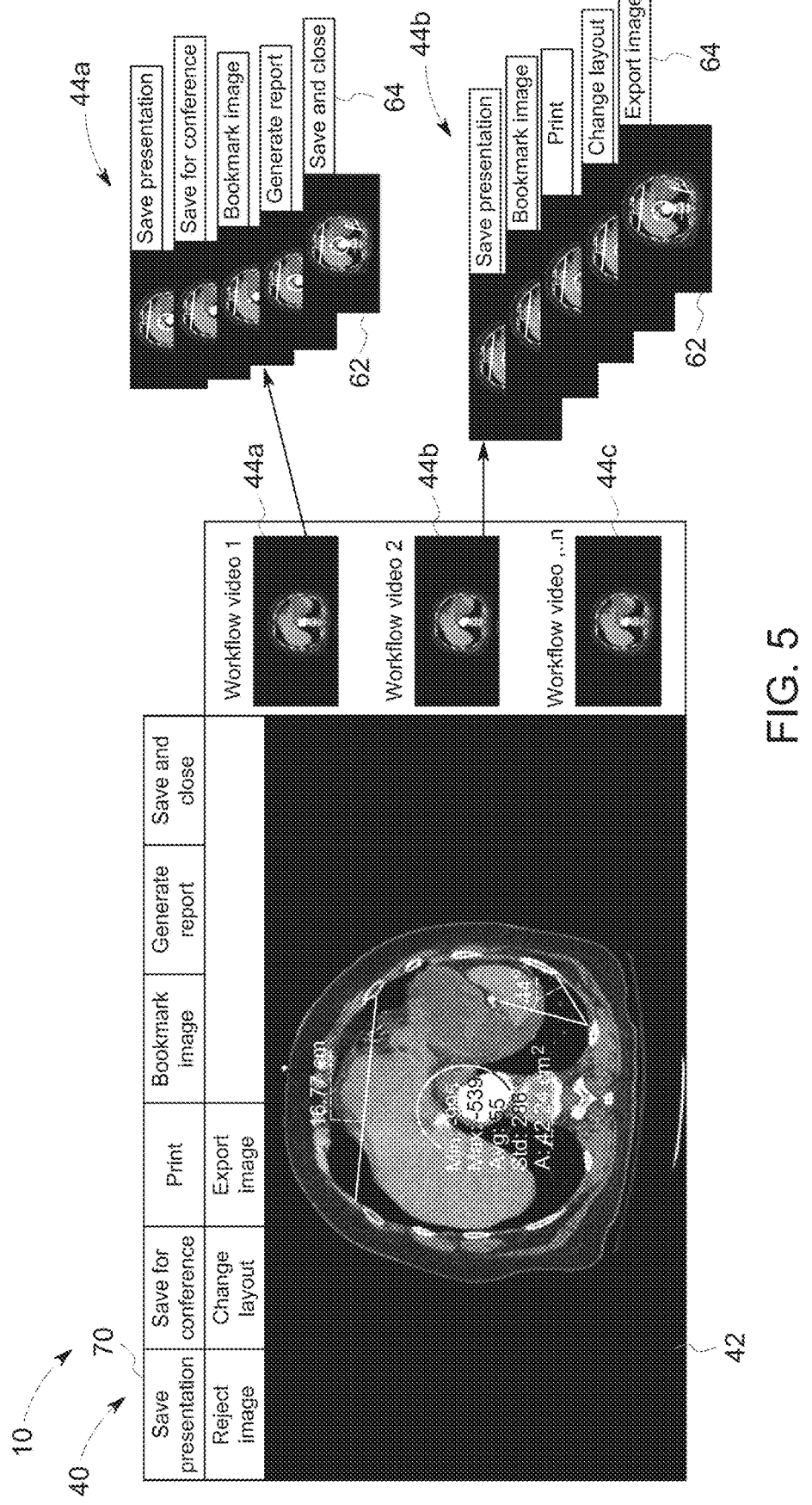
FIG. 5 illustrates a schematic diagram of the GUI of FIG. 2 displaying image data and one or more workflow videos, in accordance with embodiments described herein.

FIG. 5 is a schematic illustration of the GUI 40 displayed on the workstation 10, in accordance with aspects of the present disclosure. The illustrated GUI 40 is substantially similar to the GUI 40 described with respect to FIG. 2, except that the illustrated GUI 40 includes image data 70 selected by the operator and one or more buttons 72 populating the action panel 46.

As described herein, the operator may select image data 70 for review on the workstation 10. The illustrated image data 70 is a CT chest image in this example, but may be any suitable imagery. The operator may also select a button 72 from the action panel 46 to perform a workflow action on the image data 70. For example, a first button 72a may 'save a presentation,' a second button 72b may 'save the image data for a conference,' and a third button 72c may 'print the image data.'

The application 26 creates the workflow videos 44 with the displayed image data 70 and one or more actions of the action panel 46. As illustrated, each of the workflow videos 44 may display a first frame 60a on the GUI 40. The first frame 60a may include the pictorial representation 62 that may be the image data 70. In certain instances, the first frame 60a may include a caption 64 corresponding to a first action performed by the workflow application 26 in response to user selection.

In certain instances, the operator may hover a mouse over the first workflow video 44a (i.e., shift focus to the first workflow video 44a) to view the associated actions. For example, the first workflow video 44a may include five frames 60. Each frame 60 may include a pictorial representation 62 of the image data 70 and an animation associated with the action to be performed. Since the image data 70 remains constant throughout the review, the workflow video 44 may visually appear to be performing each action associated with the video on the image data 70. By way of example, the first workflow video 44 may include five frames 60. A first frame 60a may include the pictorial representation 62 with the image data 70 and an animation associated with 'save presentation," and the caption 64 'SAVE PRESENTATION." The second image frame 60b may also include the image data 70. The second frame 60b may include an animation associated with 'save for conference' and the caption 64 'SAVE FOR CONFERENCE.' The animation may include a mouse moving to the second button 72b associated with 'save for conference.' The third frame 60c may include the image data 70 and be associated with an action 'bookmark image.' The animation of the third frame 60c may include a mouse hovering over the button 72 of the action panel 46 associated with bookmark image. In another example, the animation of the third frame 60c may include selecting a bookmark icon located within the viewing space 42. A fourth frame 60d may be associated with generating a report and a fifth frame 60e may be associated with saving and closing the image data.

In another example, a second workflow video 44b may include five frames 60. The first frame 60a may be associated with the action of saving a presentation, a second frame 60b may be associated with the action of bookmarking an image, a third frame 60c may be associated with the action of printing the image, a fourth frame 60d may be associated with the action of changing a layout of the image, and a fifth frame 60e may be associated with the action of exporting the image.

In an embodiment, the each frame 60 of the workflow video 44 may appear to be updated with the action of the step. As such, the workflow video 44 may visually appear to be performing the workflow actions on the image data. For example, a first frame 60a may be associated with changing a layout. Then, a second frame 60b may include a pictorial representation 62 with an altered image data 70, such as image data with changed layout. As such, the operator may quickly and efficiently understand the actions associated with the workflow video.

Figure 6:
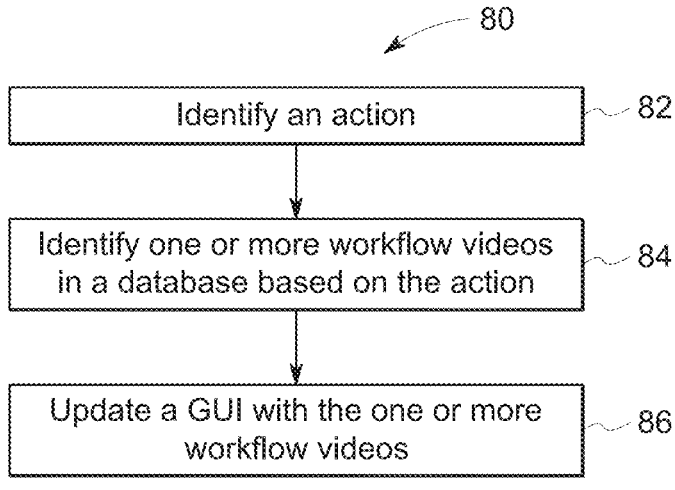
FIG. 6 illustrates a flow chart of an example method of the workflow application for identifying one or more workflow videos for display on the review station of FIG. 1, in accordance with embodiments described herein.

FIG. 6 illustrates a flow chart of a method 80 for the application 26 to update the workflow videos 44 presented on the GUI 40, in accordance with aspects of the present disclosure. One or more steps of the illustrated method 80 may be performed in a different order from the order depicted in FIG. 6 and/or simultaneously (e.g., in parallel) by the application 26.

At block 82, the application 26 may identify an action being performed. To review image data, the operator may use an input device communicatively coupled to the I/O ports 22 of the workstation 10 to perform one or more actions. The workstation 10 may display the GUI 40 and the operator may use the action panel 46 of the GUI 40 to select image data for review. The operator may then use the action panel 46 to select actions to perform on the image data, such as annotating, labelling, sending, saving, and so on. While the operator manually performs the actions, the application 26 may monitor the actions. In other words, the application 26 may identify an action being performed by the operator to identify workflow videos 44 to automate actions for the operator.

At block 84, the application 26 may identify one or more workflow videos 44 in a database 30 based on the action. For example, the application 26 may identify the action as "generate a report." The application 26 may predict the next actions of the user and present a list of workflow videos 44 on the GUI 40. To this end, the application 26 may identify one or more workflow videos 44 stored in the database 30 related to "generating a report." In certain instances, the application 26 may identify any workflow videos 44 with a frame 60 related to "generating a report." In other instances, the application 26 may identify subsequent actions the operator performs after "generating a report." After identifying the workflow videos 44, the application 26 may also identify a number of times each of the workflow videos 44 have been previously executed or a probability that the operator may execute each of the workflow videos 44. In this way, the application 26 may order the workflow videos 44 based on those most preferred (e.g., most often selected) by the operator to those least preferred (e.g., least often selected) by the operator. In another example, the application 26 may identify workflow videos 44 tagged with generating a report. The identification may be executed via machine-learning routines. As a result, the application 26 learns the preferences of the operator (enabling independence from human effort).

Additionally or alternatively, the application 26 may identify one or more workflows with the identified action. For example, the historical workflow data stored in the database 30 may include workflow sequences (e.g., two or more sequential actions). The application 26 may identify one or more workflow sequences associated with the action. Then, the application 26 may generate one or more workflow videos with the one or more workflow sequences in real time or near-real time with the displayed image data 70 within the viewing space 42.

At block 86, the application 26 may update the GUI 40 with the identified and/or generated workflow videos. As described with respect to FIG. 2, the application 26 may update the workflow videos 44 displayed to predict the operator's next actions. The workflow videos 44 may be prioritized in an order from most likely to be selected to least likely to be selected. In this way, the application 26 may save the operator time to view the workflow videos 44 and select a workflow video 44.

Figure 7:
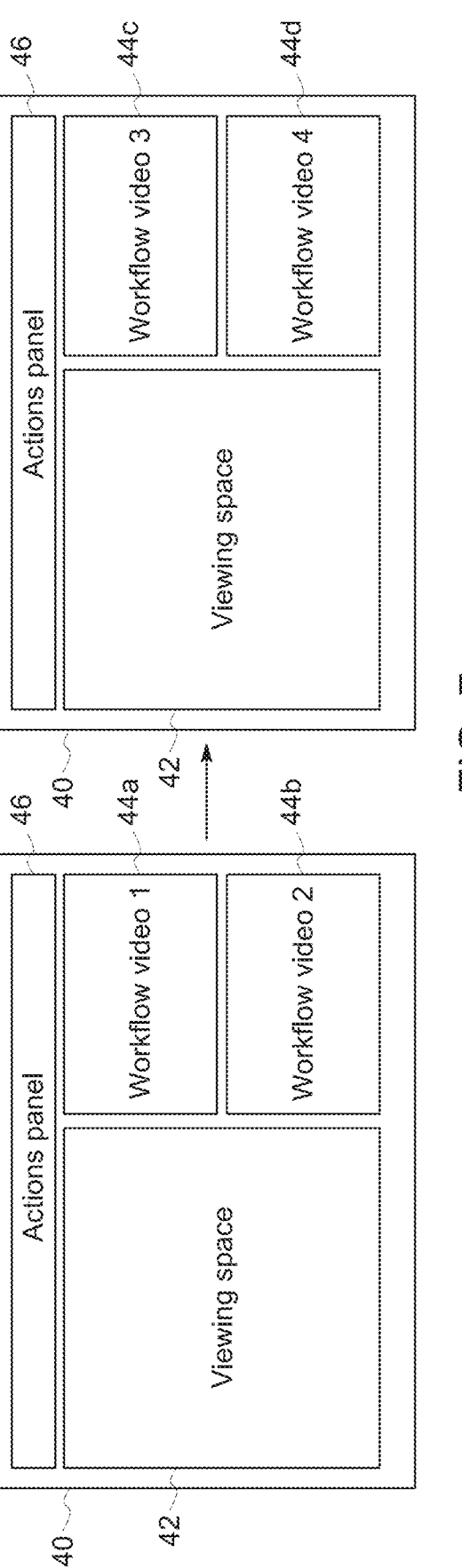
FIG. 7 illustrates a schematic diagram of the GUI of FIG. 2 updating one or more selectable workflow videos in response to an action performed on the review station of FIG. 1, in accordance with embodiments described herein.

With the preceding in mind, FIG. 7 is a schematic illustration of the application 26 updating workflow videos 44 displayed on the GUI 40 in response to operator actions, in accordance with aspects of the present disclosure. The GUI 40 may be displayed on the display 24 of the workstation 10 for the operator to perform a study or a review of image data. As illustrated, the GUI 40 may display a first workflow video 44a and a second workflow video 44b. The first workflow video 44a may be different from the second workflow video 44b and prioritized for the operator based on probability of selection by the operator. The application 26 may determine the probability of selection by the operator based on historical workflow data associated with the operator profile.

As described herein, the operator may perform an action on the image data using the action panel 46 of the GUI 40. In certain instances, the image data may not have changed based on the action (e.g., generate a report, save, download, send). In other instances, the image data may have changed based on the action (e.g., annotate, label). Regardless of whether the image data has changed, the application 26 may identify one or more workflow videos 44 in response to the action being performed and populate or update the GUI 40 with one or more new workflow videos 44. Additionally or alternatively, the application 26 may identify one or more workflow sequences in response to the action being performed and generate one or more workflow videos 44 for populating the GUI 40. For example, the GUI 40 may display a third workflow video 44c and a fourth workflow video 44d, which may be different from the first workflow video 44a and the second workflow video 44b.

In an example, the operator may manually perform an action by selecting a button from the action panel 46. The application 26 may identify the action being performed by the operator and identify one or more workflow videos 44 in the database 30 based on the action. To save the operator time and interactions, the application 26 may update the GUI 40 with the identified workflow videos 44.

In another example, the operator may select a workflow video 44 and the application 26 may sequentially perform one or more actions associated with the workflow video 44. The application 26 may identify the last action of the workflow video 44 and identify one or more workflow videos 44 in the database 30 based on the last action. The application 26 may simultaneously perform the actions of the workflow video 44 and update the GUI 40 with the identified videos. As such, the operator may continue their study after the application 26 has completed the actions of the selected workflow video 44.

Figure 8:
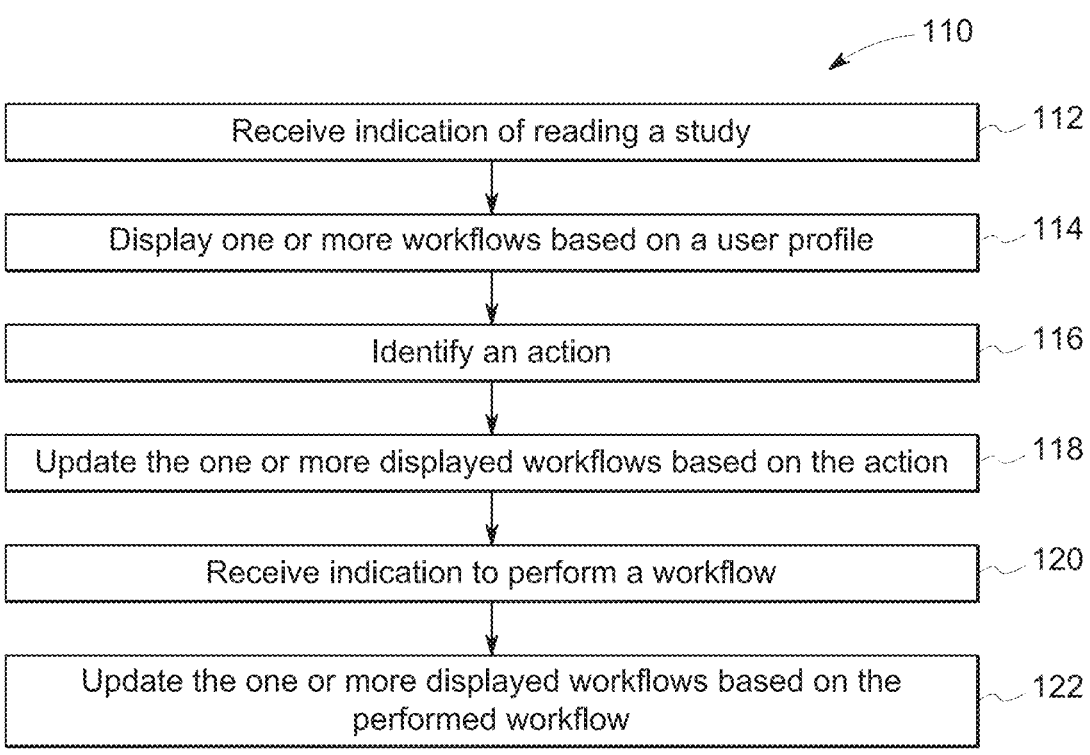
FIG. 8 illustrates a flow chart of an example method of the workflow application updating the one or more workflow videos displayed on the review station of FIG. 1, in accordance with embodiments described herein.

FIG. 8 illustrates a flow chart of a method 110 for updating workflow videos 44 of the GUI 40 in response to user input, in accordance with aspects of the present disclosure. For example, the application 26 may monitor actions selected by the operator during review of the image data. Then, the application 26 may update the workflow videos 44 presented to the operator. In this way, the application 26 may automate certain actions for the operator, thereby decreasing turnaround time and operational costs. One or more steps of the illustrated method 110 may be performed in a different order from the order depicted in FIG. 8 and/or simultaneously (e.g., in parallel) by the application 26.

At block 112, the application 26 may receive user input (e.g., selection by the user, user input) of reading a study. For example, the operator may enter login information to the workstation 10 and the application 26 may identify an operator profile based on the login. Further, the operator may use the action panel 46 to select image data for display in the viewing space 42. The application 26 may identify the action to select image data and identify that a study is being performed.

The application 26 may identify one or more workflow videos 44 to populate the GUI 40 based on the operator profile at block 114. The operator profile may include historical workflow data of previous actions performed by the operator. The application 26 may identify workflow videos 44 in the database 30 based on the historical workflow data. For example, the operator may repeatedly open image data and annotate one or more regions of interest within the image data. As such, the application 26 may present a workflow video with the steps of annotating the one or more regions of interest on the image data. In another example, the application 26 may identify profiles similar to the operator (e.g., department, institution, seniority) and use historical workflow data from other profiles to identify the workflow videos 44 populating the GUI 40.

In certain instances, the operator may perform an action using the action panel 46. At block 116, the application 26 may identify an action similar to block 82 described with respect to FIG. 4. For example, the operator may annotate the image data and the application 26 may identify the annotation as the action being performed. In another example, the operator may label areas for reprocessing and the application 26 may identify the labelling as the action.

In response to the action, the application 26 may update the one or more displayed workflows at block 118, similar to block 86 described with respect to FIG. 4. For example, the application 26 may populate the GUI 40 with the identified workflow videos 44.

At block 120, the application 26 may receive an indication (e.g., a selection by the user of a workflow video) to perform a workflow. For example, the operator may select a workflow video 44 from the list of workflow videos. The application 26 may receive the selection and sequentially perform the actions associated with the workflow video 44 without additional user input. In certain instances, the operator may start reviewing subsequent image data. In this way, the operator may decrease an amount of time needed to review image data, increase turnover, and decrease operational costs. Furthermore, having the application 26 perform one or more actions may also reduce or otherwise limit human error and may increase quality control of reviews by consistently performing the actions in the same way.

At block 122, the application 26 may update the one or more displayed workflow videos based on the performed workflow. That is, the application 26 may update the list of workflow videos 44 displayed on the GUI 40 in response to completing the workflow. For example, the application 26 may identify workflow videos associated with the last action of the workflow video 44 and update the GUI 40 with the identified videos. As such, the operator may view the workflow videos 44 and identify a subsequent workflow to be performed.

Although the method 110 is described in a particular order, it should be noted that the method 110 may be performed in any suitable order and is not limited to the order presented herein. It should also be noted that although each block is described with respect to the method 110 as being performed by the workstation 10, other suitable workstations may perform the methods described herein.

Figure 9:
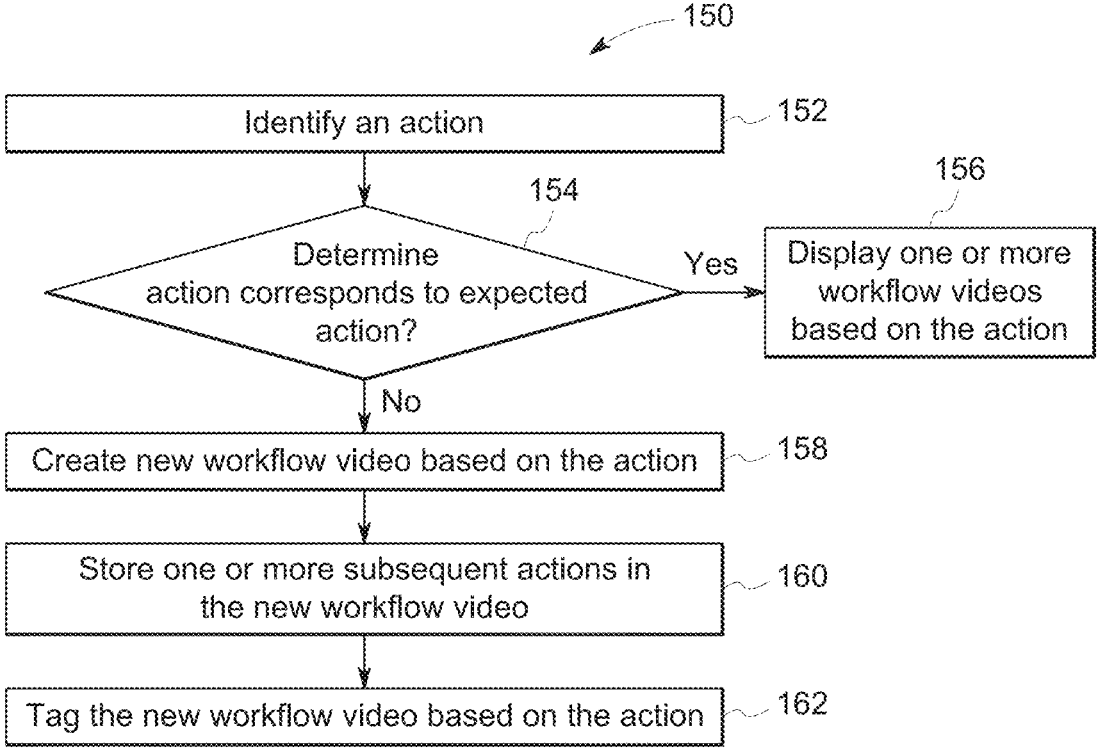
FIG. 9 illustrates a flow chart of an example method for identifying or creating a workflow video display on the review station of FIG. 1, in accordance with embodiments described herein.

FIG. 9 illustrates a flow chart of a method 150 of the application 26 for determining if an action corresponds to an expected action and/or creating new workflow videos 44, in accordance with aspects of the present disclosure. In certain instances, the operator may perform actions that deviate from an expected action (e.g., from historical workflow data) and/or workflows. In an embodiment, the application 26 may determine one or more workflow sequences from the historical workflow data and generate the workflow videos 44 based on the workflow sequences. For example, a first frame 60a of the workflow video may correspond to a first action of the workflow sequence, a second frame 60b of the workflow video may correspond to a second action of the workflow sequence, and so on. The application 26 may record the deviated actions for a new workflow video 44 and/or a new workflow sequence. In this way, the application 26 may learn actions and/or preferences of the operator and predict future actions to improve performance.

At block 152, the application 26 may identify an action, similar to block 82 described with respect to FIG. 6 and block 116 described with respect to FIG. 8. At block 154, the application 26 may determine if the action corresponds to an expected action. For example, the application 26 may predict a subsequent action to identify one or more workflow videos 44 of interest to the operator. In another example, the application 26 may identify one or more workflow sequences that may be performed by the operator subsequent to the identified action. The predicted subsequent action may be the expected action. For example, the application 26 may compare the identified action to the historical workflow data to predict the subsequent action (e.g., an expected action). In another example, the application 26 may compare the identified action to actions of workflow videos 44 and/or workflow sequences to identify the expected action.

If the identified action corresponds to the expected action, then at block 156, the application 26 populate the GUI 40 with the one or more workflow videos for display based on the action. For example, the application 26 may identify one or more workflow videos 44 with the expected action and create a list prioritizing the one or more videos. In another example, the application 26 may generate one or more workflow videos 44 with the image data 70 and actions of one or more identified workflow sequences. The application 26 may then populate the GUI 40 with the list of workflow videos 44.

If the action does not correspond to the expected action, at block 158, the application 26 may create a new workflow video based on the identified action. Additionally or alternatively, the application 26 may store a new workflow sequence based on the identified action. For example, if the operator deviates from the expected action, then the application 26 may screen capture and/or store subsequent actions to create a new workflow for the operator. The application 26 may also learn the point of deviation. In this way, the application 26 may adjust a prediction for future reviews and learn the workflows of the respective operator.

At block 160, the application 26 may store one or more subsequent actions in the new workflow. The application 26 may screen capture the operator's subsequent actions. The screen capture may be a video or a still image of the subsequent action. In another example, the application 26 may store the subsequent actions in the database 30 (e.g., as historical workflow data) and identify an associated frame 60. The application 26 may add the frame to the workflow video 44 and create a new workflow video 44. Additionally or alternatively, the application 26 may store the deviated action and subsequent actions as part of a workflow sequence in the database 30. In this way, the application 26 may learn workflow operations of the operator and optimize the workflow operations for the operator.

At block 162, the application 26 may tag the new workflow video 44 based on the action. As such, the application 26 may present the new workflow video 44 the next time the operator performs the deviated action. As such, the application 26 may accurately predict subsequent actions of the operator.

Although the method 150 is described in a particular order, it should be noted that the method 150 may be performed in any suitable order and is not limited to the order presented herein. It should also be noted that although each block is described with respect to the method 150 as being performed by the workstation 10, other suitable workstations may perform the methods described herein.

Figure 10:
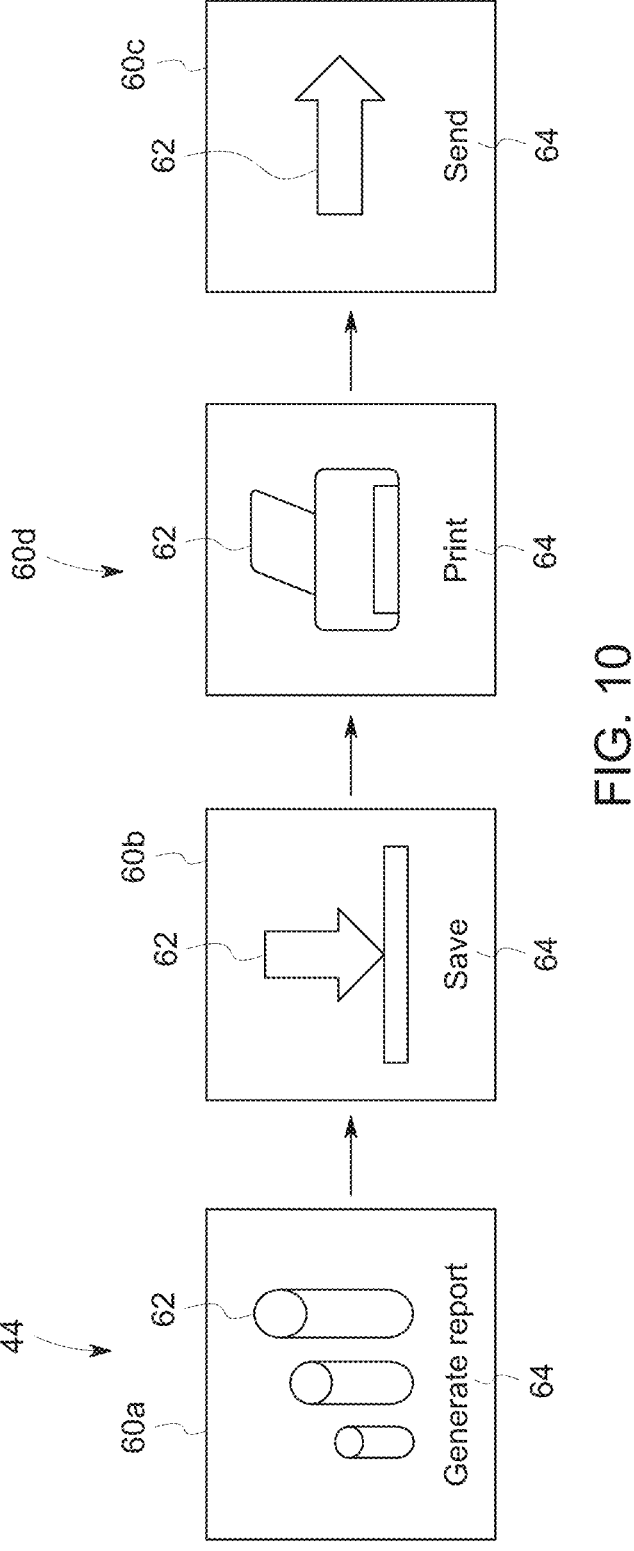
FIG. 10 illustrates a schematic diagram of a workflow video created by the workflow application for display on the review station of FIG. 1, in accordance with embodiments described herein.

FIG. 10 is a schematic illustration of the application 26 creating a new workflow video 44 based on the operator's actions deviating from an expected action, in accordance with aspects of the present disclosure. The workflow video 44 of FIG. 8 is similar to the workflow video 44 described with respect to FIG. 4 except a fourth frame 60d is added. If the operator deviates from an expected action, the application 26 may monitor subsequent actions and create a new workflow video 44 based on the deviation, such as by adding a step and corresponding frame 60 so as to make a new workflow video 44.

For example, the operator may generally generate a report, save the image data, and send the image data. In certain instances, the operator may change workflow operations to generate a report, save the image data, print the image data, and send the image data. The application 26 may identify the additional action of "print the image data" and include a fourth frame 60d to the workflow video 44. The fourth frame 60d may include a pictorial representation 62 as a printer and a caption 64 reading. "PRINT."

The application 26 may tag the new workflow video 44 with "SAVE," since the operator deviated after this action. As such, in subsequent predictions, the application 26 may identify the new workflow video in response to receiving user input to perform the action "SAVE."

Figure 11:
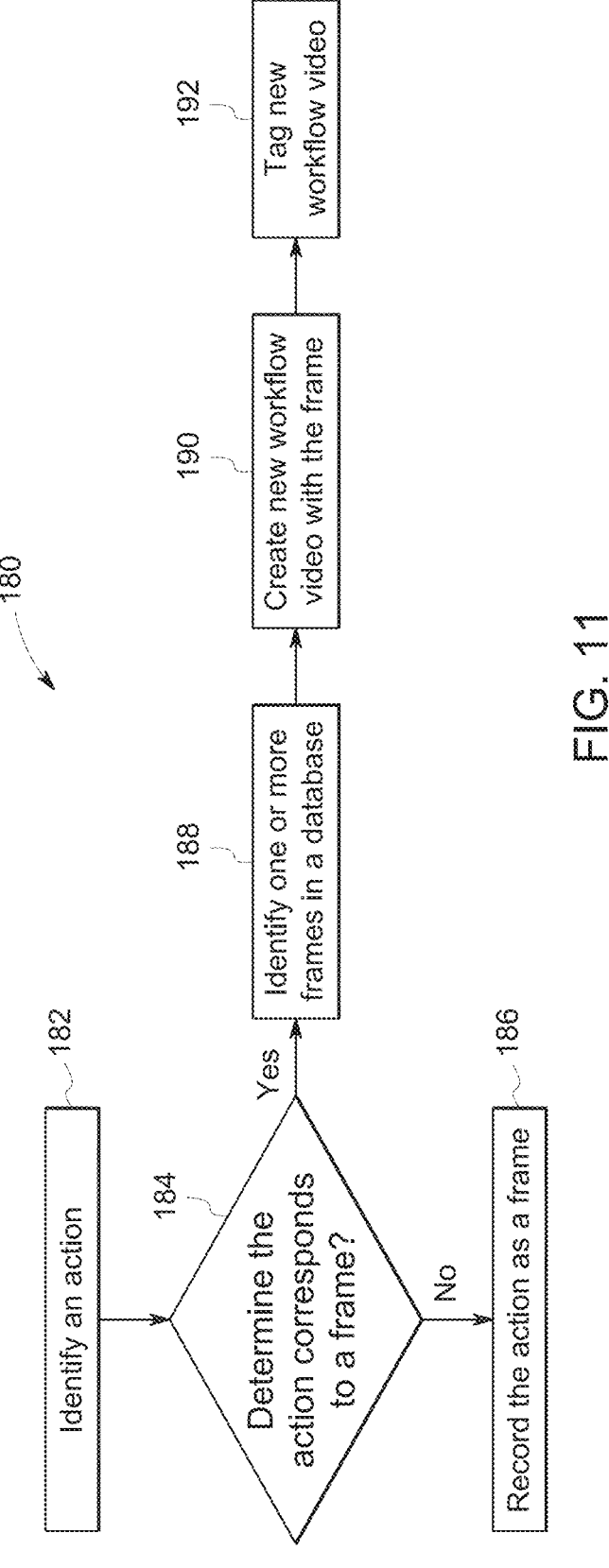
FIG. 11 illustrates a flow chart of an example method of the workflow application creating a new workflow video by creating one or more video fragments; in accordance with embodiments described herein.

FIG. 11 is a flow chart of an embodiment of a method 180 for creating a new workflow video 44, in accordance with aspects of the present disclosure. If the operator deviates from an expected action, the application 26 may record subsequent actions of the operator to create a personalized workflow video 44 for the operator. In certain instances, the database 30 may include a frame 60 illustrating the deviated action and the application 26 may create a new workflow video 44 with the frame 60. However, in certain instances, the database 30 may not include a frame 60 illustrating the deviated action. For example, the workstation 10 may be updated with new actions and the frames 60 in the database 30 may not have been updated. Still in other instances, it may be beneficial for the application 26 to record one or more actions of the operator to create personalized workflow videos 44 for the operator. As such, the application 26 may create new frames 60 and store the frames 60 in the database 30.

At block 182, the application 26 may identify an action, similar to block 82 described with respect to FIG. 6 and block 152 described with respect to FIG. 9. At block 184, the application 26 may determine if the action corresponds to a frame 60. In certain instances, the identified action may deviate from an expected action. As such, the application 26 may search one or more frames stored in the database 30 for a frame 60 associated with the deviated action.

If the action does not correspond to a frame, then at block 186, the application 26 may record the action as a new frame 60. For example, the application 26 may capture a still image or video data of the deviated action. The application 26 may tag the captured image as a new frame 60 with a string of text associated with the image. For example, if the operator performs an action, such as adjusting the contrast, the application 26 may label the new frame 60 as "CONTRAST." As such, the application 26 may create subsequent workflow videos 44 with the new frame 60.

If the subsequent action does correspond to a frame 60, then at block 188, the application 26 may identify the frame 60 in the database 30. For example, the application 26 may use the tags of the frames 60 to identify a frame 60 corresponding to the deviated action. In another example, the application 26 may use pictorial representations 62 to identify the deviated action. Still in another example, the application 26 may identify one or more frames 60 associated with the deviated action. Over time, the application 26 may screen capture one or more actions, as performed by the operator, to create personalized workflow videos 44. As such, the database 30 may include multiple frames 60 associated with one action.

At block 190, the application 26 may create a new workflow video 44 with the frame 60. For example, the application 26 may link the frame 60 associated with the deviated action to one or more frames 60 to create the workflow video 44. At block 192, the application 26 may tag the new workflow video 44, similar to block 162 described with respect to FIG. 7.

Although the method 180 is described in a particular order, it should be noted that the method 180 may be performed in any suitable order and is not limited to the order presented herein. It should also be noted that although each block is described with respect to the method 180 as being performed by the workstation 10, other suitable workstations may perform the methods described herein.

Technical effects of the disclosed embodiments include providing systems and methods that automatically perform a workflow including two or more actions on image data. Providing the workflow as an actionable video allows the operator to easily identify the actions to be performed and to automate two or more actions that would otherwise require the operator to manually perform the actions. The automation of the workflow enables the operator to review image data more quickly, more efficiently, and with less human error. By predicting the operator's subsequent actions, the disclosed techniques may reduce an amount of time needed to review image data. In addition, the disclosed techniques create a list of workflow videos that are prioritized based on preferences of the operator and/or of other similar operators. In this way, the operator may spend less time identifying an appropriate workflow video, thereby further reducing time spent reviewing the image data. As such, the operator may reduce turnaround time and increase efficiency.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A system comprising:
a database comprising historical workflow data associated with a review of clinical images, a plurality of workflow videos, and a plurality of frames;
a radiology review station in communication with the database and configured to:
populate a graphical user interface (GUI) with a clinical image and one or more workflow videos of the plurality of workflow videos; and
receive an input corresponding to selection of a workflow video of the one or more workflow videos, wherein the workflow video corresponds to two or more actions to be performed on the clinical image during the review of the clinical images; and
a workflow application comprising routines executed by a processor of the radiology review station and communicatively coupled to the database, wherein the workflow application is configured to:
adjust the clinical image by performing the two or more actions corresponding to the workflow video without user intervention in response to receiving the selection;
identify one or more additional workflow videos for display on the GUI in response to adjusting the clinical image;
determine a likelihood of selection for each of the one or more additional workflow videos based on a user profile;
update the GUI with the one or more additional workflow videos, wherein the one or more additional workflow videos are ordered from a highest likelihood of selection to a lowest likelihood of selection;
receive a second input corresponding to an action to be performed on the clinical image;
determine the action does not correspond to an expected action;
creating a first frame of the set of frames corresponding to the action;
creating one or more frames of the set of frames based on one or more subsequent actions after the action;
generating a new workflow video based on the first frame and the one or more frames; and
tagging the new workflow video based on the action.

2. The system of claim 1, wherein the one or more frames correspond to the one or more subsequent actions to be performed by the workflow application without user intervention.

3. The system of claim 1, wherein each frame of the plurality of frames comprises an animation corresponding to an action to be performed by the workflow application without user intervention.

4. A method comprising:

populating, via a processor, a graphical user interface (GUI) with a medical image and a first set of workflow videos based on a user profile;

receiving, via the processor, a selection of a workflow video of the first set of workflow videos, wherein the workflow video corresponds to two more actions to be performed on the medical image without user intervention;

identifying, via the processor, a second set of workflow videos for display on the GUI in response to receiving the selection of the workflow video;

determining, via the processor, a likelihood of selection for each of the second set of workflow videos based on the user profile;

updating, via the processor, the GUI with the second set of workflow videos, wherein the second set of workflow videos are ordered from a highest likelihood of section to a lowest likelihood of selection; and receiving, via the processor, a first input corresponding to an action performed on the medical image;

determining, via the processor, that the first input does not correspond to an expected action;

recording, via the processor, one or more frames corresponding to one or more subsequent actions performed in response to the determination;

tagging, via the processor, the one or more frames with a respective name of the one or more subsequent actions; and storing, via the processor, the one or more frames.

5. The method of claim 4, comprising:

receiving, via the processor, a second input of an action to be performed on or performed on the medical image;

determining, via the processor, that the second input corresponds to an expected action; and selecting, via the processor, a third set of workflow videos from a plurality of workflow videos stored in a database based on the action.

6. The method of claim 4, comprising:

creating, via the processor, a new workflow video comprising the one or more frames.

7. A non-transitory, computer-readable medium comprising computer-readable code, that when executed by one or more processors, causes the one or more processors to perform operations comprising:

populating a graphical user interface with a medical image and a list of workflow videos based on a user profile;

receiving a first input of selecting a workflow video of the list of workflow videos, wherein the workflow video corresponds to two or more actions performed on or to be performed on the medical image without user intervention;

identifying one or more additional workflow videos for display on the GUI in response to receiving the first input;

determining a likelihood of selection for each of the one or more additional workflow videos based on the user profile;

updating the list of workflow videos concurrently displayed with the medical image based on the workflow video, wherein the one or more additional workflow videos are ordered from a highest likelihood of selection to a lowest likelihood of selection;

receiving a second input corresponding to an action performed on the medical image;

determining that the second input does not correspond to an expected action;

recording one or more frames corresponding to one or more subsequent actions performed in response to the determination; and storing the one or more frames.

8. The non-transitory, computer-readable medium of claim 7, wherein the operations comprise:

creating a new workflow video comprising the one or more frames;

tagging the new workflow video based on a name of the one or more subsequent actions; and associating the new workflow video with the user profile.

9. The system of claim 1, wherein the radiology review station is configured to:

receive a third input corresponding to interaction with a second workflow video of the one or more additional workflow videos, wherein the second workflow video comprises two of more frames of the plurality of frames corresponding to two or more actions to be performed on the clinical image without user intervention; and initiate display of the plurality of frames based on the third input.

10. The method of claim 6, comprising:

generating, via the processor, each frame of the one or more frames based on the one or more subsequent actions.

11. The method of claim 4, comprising:

generating, via the processor, a report based on the medical image and the workflow video; and sending, via the processor, the medical image based on the workflow video.

12. The system of claim 1, wherein the user profile comprises a number of selections associated with each of the plurality of workflow videos, wherein a higher number of selections corresponds to a higher likelihood of selection, and wherein a lower number of selections corresponds to a lower likelihood of selection.

13. The system of claim 1, wherein the workflow application is configured to implement a machine learning technique to:

predict a subsequent action based on the user profile; and identify the one or more additional workflow videos based on the predicted subsequent action, wherein each of the one or more additional workflow videos comprises a first frame corresponding to the predicted subsequent action.

14. The non-transitory, computer-readable medium of claim 7, wherein the user profile comprises a number of selections associated with each of the one or more additional workflow videos, and wherein the order comprises displaying a first video of the one or more additional workflow videos associated with a highest number of selections first.

15. The system of claim 1, wherein the workflow videos comprise pictorial representations of the actions to be performed on the clinical image.

16. The system of claim 1, wherein the workflow videos comprise recordings of the actions to be performed on the clinical image.

17. The system of claim 1, wherein the radiology review station is configured to populate a second GUI with a second clinical image and a second plurality of workflow videos, wherein the workflow application is configured to adjust the second clinical image in response to receiving a second selection of a second workflow video of the second plurality of workflow videos.

18. The system of claim 1, wherein the radiology review station is configured to receive an additional input indicative of selection of an additional workflow video of the one or more additional workflow videos, wherein the workflow application is configured to initiate display of frames of the additional workflow video in response to the additional input.

19. The system of claim 18, wherein the additional input comprises an indication of a cursor hovering over the additional workflow video.

\* \* \* \* \*